United States Patent [19]

Fein

[11] Patent Number: 4,912,060

[45] Date of Patent: Mar. 27, 1990

[54] METHOD AND APPARATUS FOR ELECTRICAL TESTING OF MEMBRANES

[75] Inventor: Harry Fein, Guilford, Conn.

[73] Assignee: World Precision Instruments, Inc., New Haven, Conn.

[21] Appl. No.: 312,043

[22] Filed: Feb. 17, 1989

[51] Int. Cl.4 ............................................. C12M 1/34
[52] U.S. Cl. .................................... 435/291; 128/734; 204/403; 204/409; 204/414
[58] Field of Search ................ 435/291; 204/414, 403, 204/409; 128/639, 734

[56] References Cited

U.S. PATENT DOCUMENTS 3,833,495  9/1974  Grubb ................................. 204/414
4,686,190  8/1987  Cramer et al. ....................... 435/291

Primary Examiner—Carroll B. Dority
Attorney, Agent, or Firm—Chilton, Alix & Van Kirk

[57] ABSTRACT

A method and apparatus for electrical testing of membrane tissue employs a pair of rack sections which have cavities for receiving opposing end portions of the culture cup. The culture cup and rack sections are clamped together to form test chambers at opposing sides of the cup substrate on which the experimental tissue is grown. Electrode cartridges are inserted into axial bores of the receiving cavities to provide a test current through the membrane tissue. Integral connectors connect with conduits for passing irrigation streams through the test chambers.

26 Claims, 3 Drawing Sheets 4,912,060

METHOD AND APPARATUS FOR ELECTRICAL TESTING OF MEMBRANES

BACKGROUND OF THE INVENTION

(1) FIELD OF THE INVENTION

This invention relates to methods and apparatus for conducting electrical measurements of epithelial tissue. More particularly, the present invention relates to methods and apparatus for making electrical measurements upon membrane samples.

(2) PRIOR ART

The technology associated with making electrical measurements upon epithelial tissue has conventionally involved employing a test chamber. Pieces of epithelia are positioned between two sections of a cylindrical chamber. Aerated fluid is circulated through the test chamber to maintain the tissue in a living state. Each chamber section conventionally has at least four ports. Two ports connect with conduits for circulating aerating fluids through the chamber. In addition, there are two ports which provide electrical communication with exterior metal electrodes. Gel-electrolyte "salt bridges", which are tubes filled with agar gel saturated with a salt solution, connect with metal electrodes. The metal electrodes are disposed in beakers which contain a salt solution. In the conventional electrical measurement technology to which the invention relates, each of the chamber sections is connected to a air of electrodes in the circulating fluid system. Because of the potentially toxic effect of metal and metallic compounds upon the test subject, metallic electrodes are usually not directly introduced into the chambers. The gel-filled salt bridge ordinarily retards the transport of metal or metal products to the tissue to be tested. Four electrodes are normally employed in the conventional testing apparatus. One electrode in each of the chamber sections measures the voltage between the chamber sections, and a second pair of electrodes is employed to establish current flow through the experimental tissue disposed between the chamber sections.

Recent advances in the technology of epithelial culture and growth have involved growing the epithelia in plastic cell culture cups having a diameter which may range from approximately 5 to 30 millimeters. The culture cups include paper or porous bottom structures upon which the epithelia cells are induced to grow in a skin-like layer. The technology of electrical testing of the epithelia has accordingly adapted to the widespread usage of culture cups by the use of apparatus and methods which involve inserting the tissue culture cup with the tissue to be tested inside the conventional test chamber. However, the insertion of a tissue culture cup into a conventional testing chamber presents a number of here-to-for unsolved problems. First, the apparatus is relatively expensive and difficult to fabricate. Secondly, the apparatus conventionally is only adapted to accommodate a single sample at a time thereby resulting in serial sample analyses and subsequent serialization which is extremely time consuming. In addition, the relatively long gel-filled salt bridge tubes which lead to the electrodes are unwieldy, time consuming to prepare and become easily dislodged from the testing apparatus. Also, because the long salt bridge tubes introduce a relatively high electrical resistance to the current pathway, a relatively high voltage is required in order to force the current through the membrane sample. Use of a high voltage is undesirable because it is inconvenient electronically, most modern test equipment requiring low voltage at the input terminals, and because it presents a shock hazard.

SUMMARY OF THE INVENTION

Briefly stated, the invention in a preferred form comprises a novel rack for electrically testing membrane tissue which is disposed across a substrate of a culture cup. A first rack section defines a cavity which receives one end of the culture cup to form a first test chamber located on one side of the cup substrate. A second rack section defines a second cavity which receives the second end of the culture cup to form a second test chamber located on the other side of the cup substrate. Connectors are provided for connecting with conduits forming irrigation paths through the first and second test chambers. Electrode cartridges are insertable into the test chambers. The rack sections are clamped together in cooperative relationship wherein a culture cup is received in the section cavities for retention between the rack sections.

The rack sections may be panel-like members. Sealing gaskets may be employed to seal the test chambers. The rack sections are clamped together by clamp members which have pairs of opposing edges which engage the rack sections to interlock the sections and the culture cup in an assembled relationship. A generally L-shaped conduit may extend interiorly into the test chamber. The cavities may have a stepped-cylindrical shape with a generally cylindrical protruding structure surrounding an end portion of the cavity.

The electrode cartridge includes an electrode which is disposed at a proximal end of the cartridge and a gel material which substantially fills the cartridge. The cartridge terminates in a tapered tip which is dimensioned to allow insertion of the cartridge means to provide a force fit fluid tight connection with the panel sections. The rack sections are spaced so that the cup is suspended between the rack sections. The rack sections may also be configured to simultaneously accommodate a plurality of culture cups.

The method for electrically testing membranes disposed across a cell culture cup substrate comprises forming a test chamber which is partially defined by a portion of a cup on one side of the substrate. A second test chamber partially defined by a portion of the cup on the opposing side of the substrate is also formed. Irrigation streams are passed through both of the test chambers. The test chambers are formed by inserting apposed portions of the culture cup into cavities formed in a pair of panel-like members and clamping the members together in a fluid-tight relationship.

An object of the invention is to provide a new and improved method and apparatus for electrical testing of membranes.

Another object of the invention is to provide a new and improved apparatus for efficiently electrically testing membrane grown in culture cups.

A further object of the invention is to provide a new and improved apparatus for electrical testing of membranes which apparatus is adapted for efficiently testing multiple membrane samples and is relatively easily sterilized.

A yet further object of the invention is to provide a new and improved apparatus for electrical testing of membranes which apparatus has a very efficient construction and can provide the requisite current flow through a membrane sample with a lower applied voltage when compared to previously available apparatus.

Other objects and advantages of the invention will become apparent from the drawings and the specification.

DETAILED DESCRIPTION OF THE INVENTION

Figure 1:
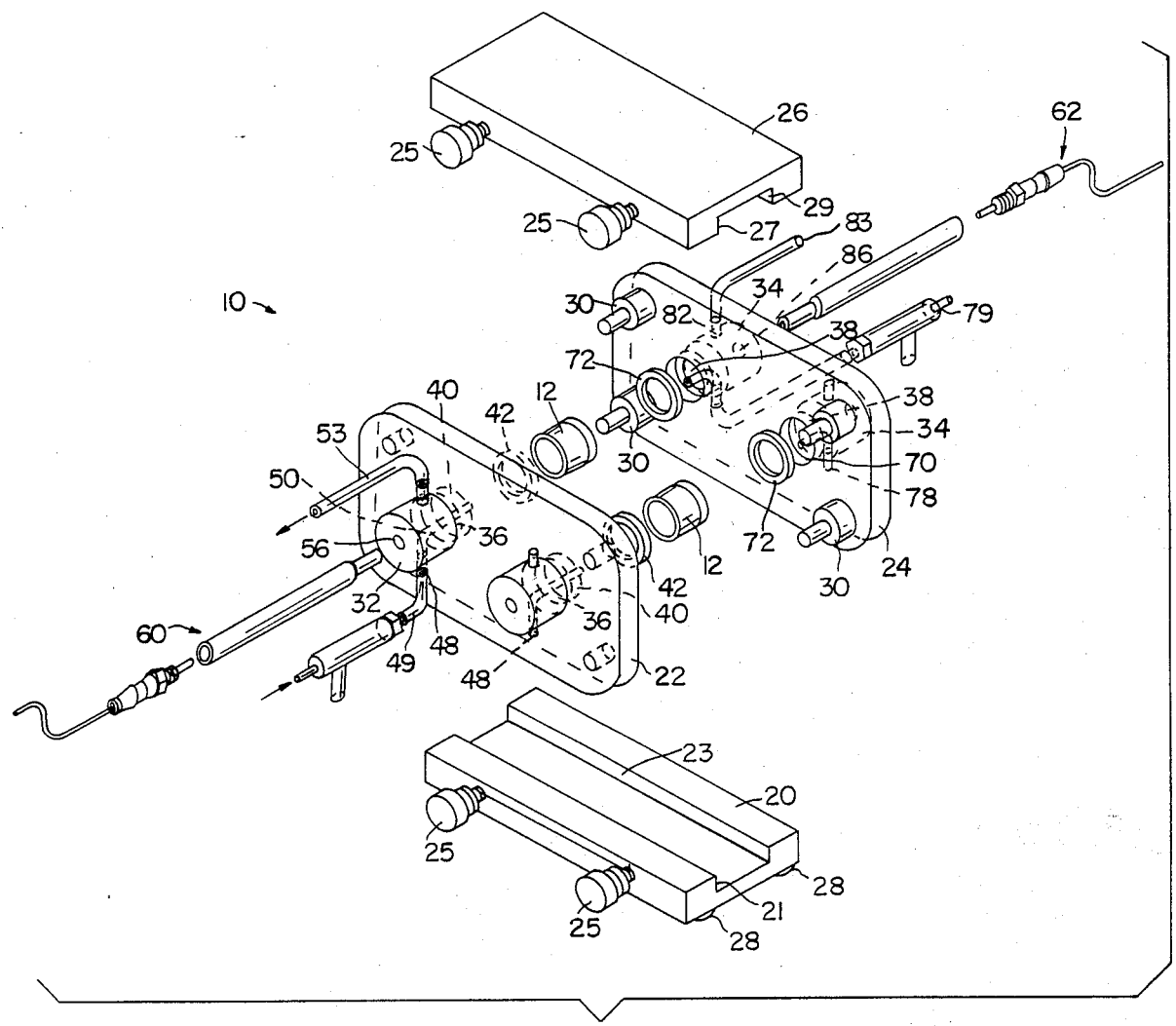
FIG. 1 is an exploded view of an apparatus for electrical testing of membranes in accordance with the present invention.
Figure 2:
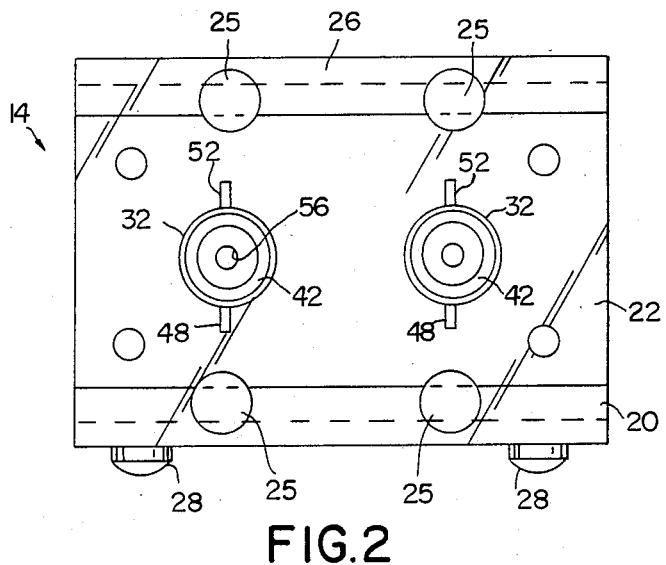
FIG. 2 is a front vie of an assembled test rack of the apparatus of FIG. 1.
Figure 3:
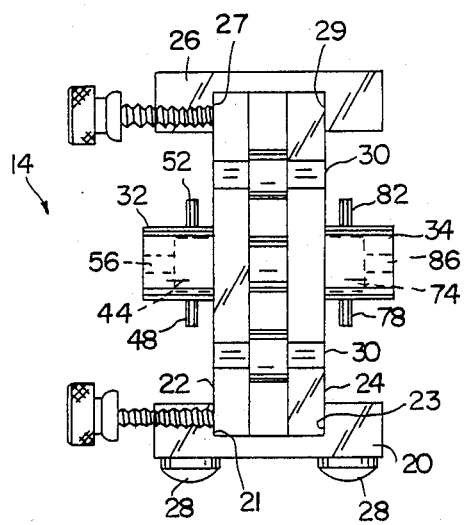
FIG. 3 is a side elevational view of the rack of FIG. 1.

With reference to the drawings, wherein like numerals represent like parts throughout the figures, an apparatus for electrical testing membranes in accordance with present invention is generally designated by the numeral 10. The method and apparatus of the present invention are directed to electrical testing of membrane-type tissue or epithelia tissue T which is grown in culture cups 12. Each culture cup includes a substrate of paper or porous material which mounts or supports the epithelia tissue T to be tested. Apparatus 10, as illustrated, is adapted to accommodate two substantially identical culture cups, although it should be appreciated that the invention may be suitably practiced in connection with any of a multiple number of such cups and with culture cups of various shapes and dimensions.

Apparatus 10 comprises test rack 14 which may be readily assembled and disassembled. The rack 14 comprises a base 20 which receives a pair of panels 22 and 24. The panels 22 and 24 are assembled in transversely spaced parallel upright relationship and secured by a cover panel 26. Support legs 28 project from the underside of the base o facilitate mounting the rack in upright relationship on a lab table or similar fixture. The base 20, front panel 22, rear panel 24 and cover 26 are electrical non-conductors which are preferably made of a clear acrylic, polycarbonate or other clear plastic. Four guide lugs 30 are insertable into alignable openings of panels 22 and 24 to facilitate assembly of the panels into a housing rack. The lugs 30 have axially spaced shoulders which engage the interior surfaces of the panels 22 and 24 to limit the sealing force applied to the cups 12.

The assembled rack 14 may hold one culture cup, two culture cups 12 as illustrated, or several cups. One or more cylindrical heads 32 (one for each culture cup) protrude from a generally planar surface portion of panel 22. Receiving cavity 36 which extends from the inner surface of the front panel 22 into the head 32 has a stepped-cylindrical form. An annular transition shoulder 40 is locate at an intermediate axial position of the cavity. The shoulder is dimensioned to receive a sealing gasket 42. Gasket 42 seals between the shoulder and the top end of the culture cup 12 to form a front test chamber 44. Accordingly, the cavity 36 is diametrially dimensioned to accommodate the culture cup and axially dimensioned to receive a top portion of the cup.

An inflow connector 48 integrally radially projects downwardly from head 32 for connecting an inflow conduit 49. An integrally formed inverted L-shaped conduit 50 extends axially into the chamber 44 to provide fluid communication between the conduit 49 and the chamber. An outflow connector 52 integrally extends radially upwardly from head 32 for connecting an outflow conduit 53. An axial bore 56 at the outer frontal end portion of the head 32 is adapted to receive a cartridge electrode assembly 60 as will be further described below.

Rear panel 24 has substantially the same general shape and features as panel 22 including one or more outwardly protruding heads 34. Likewise, receiving cavity 38 extends rearwardly from the inner surface of the rear panel 24 into the head 34 and has a stepped-cylindrical form. An annular transition shoulder 70 located at an intermediate axial position of cavity 38 seats a sealing gasket 72. Gasket 72 seals between the shoulder and the bottom of the culture cup 12 to form a rear test chamber 74. The receiving cavity 38 is diametrally dimensioned to accommodate the culture cup and is axially dimensioned to receive the bottom portion of the cup. The dimensions of panel 24 may be slightly different than the corresponding dimensions of panel 22 to accommodate dimensional and shape differences between the top and bottom portions of cell culture cup 12.

An inflow connector 78 integrally projects radially downwardly from the head 34 for connecting a inflow conduit 79. An integrally formed inverted L-shaped conduit 80 extends axially into the chamber 74 to provide fluid communication between the conduit 79 and the chamber 74. The axial extent of conduit 80 may be slightly less than that of conduit 50 so that the outlets of conduits 50 and 80 are roughly equidistantly spaced from the tissue T. An outflow connector 82 extends radially upwardly from head 34 for connecting an outflow conduit 83. An axial bore 86 at the rear outer end portion of the head 34 is adapted to receive a cartridge electrode assembly 62 which may be substantially identical to electrode assembly 60.

It will be appreciated that the panels 22 and 24 are dimensioned so that a culture cup 12 may be suitably oriented and inserted between the panels for reception in respective cavities 36 and 38. Upon clamping the panels against opposing ends of the culture cup, a pair of fluid-tight test chambers 44 and 74 are formed at opposing ends or sides of the epithelia membrane T or bottom substrate structure of the culture cup. In practice, the bottom of the cup may be initially seated against sealing gasket 72 in cavity 38. The cavity 36 is aligned with cup 12 and the front panel and rear panels are forced toward each other. Multiple pairs of alignable receiving cavities may be provided in the panels 22 and 24 as desired. Each such cavity is substantially identical in form and shape to that previously described for receiving cavities 44 and 74. However, the cavities may be suitably dimensioned in accordance with specific culture cup dimensions.

After the culture cup (or cups) has been properly positioned in the associated cavities 36 and 38 between the panels 22 and 24, the panels/cup assembly is mounted over the base 20. The cover 26 is then mounted on the top edge portions of the panels. Equidistantly spaced retention flanges 21 and 23 of the base and equidistantly spaced retention flanges 27 and 29 of the cover interiorly engage respective bottom and top outer edge portions of the panels 22 and 24 to transversely interlock the panels. Clamp screws 25 threaded at one side of the base and the cover are rotatably displaceable to engage the panels to thereby securely lock the rack in assembled relationship. The cover 26 and base 20 thus function as a pair of generally quazi-C-shaped clamps to clamp at the bottom and top edges of the panels to secure the rack including one or more culture cups 12 in an interlocking clamped fluid-tight configuration.

Figure 4:
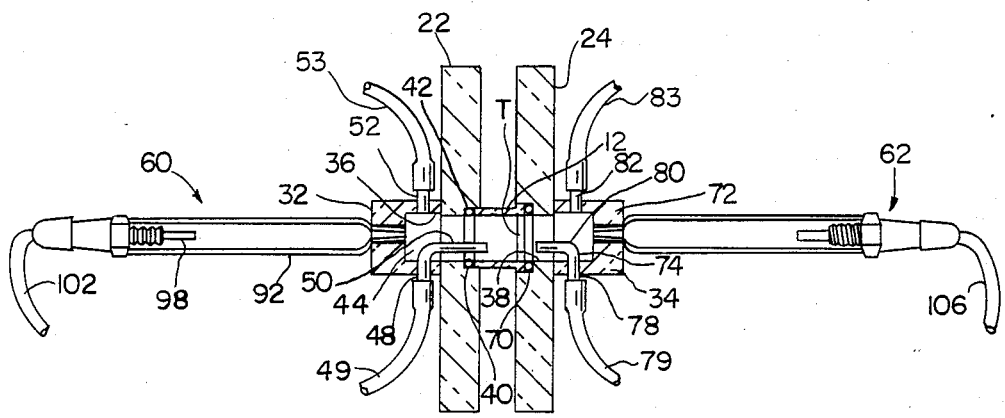
FIG. 4 is an enlarged fragmentary sectional view of the assembled apparatus of FIG. 1.

With reference to FIG. 4, the inflow conduit 49 and outflow conduit 53 for the front test chamber 44 form an irrigation path through chamber 44. An aerated salty solution is forced under pressure through the conduit 49 to fill the chamber 44 and then exit through the outflow conduit 53. A second irrigation path also conveying a pressurized aerated salty solution traverses through conduit 79, chamber 74 and conduit 83. It will be appreciated that the fluid flowing into and out of each of the chambers 44 and 74 may be electrically conductive. Thus, the apparatus 10 employs the fluid inflow channels as an electrical pathway to external salt bridge electrodes as well as for irrigation. The chamber inflow passages may be simultaneously used for sensing voltage on either side of the epithelia membrane T. The salt bridges comprise conduits filled with a gel, agar gel, for example, which is also saturated with a salt solution. The salt bridges connect with metal electrodes which are disposed in beakers filled with a salt solution. The gel-filled salt bridge functions to retard the transport of metal or metal products to the test membrane T when current flows.

For electrical measurements in the form of a so-called "short-circuit voltage clamp", the current flow through the epithelial membrane is automatically controlled and may become as great as one milli-ampere. The inner diameter of the outflow channels, through connectors 52, and 82 may typically be on the order of approximately one or two millimeters. Consequently, the electrical resistance of the outflow-current channels may be as high as fifty kilo-ohms owing to the resistivity of the saline irrigated solution. Thus, the consequent voltage drop across the outflow conduit could exceed fifty volts. In order that the voltage drops across the current pathway in chambers 44 and 74 be limited to relatively small differentials, a large diameter current path is required. The large diameter path is established by means of electrode cartridge assemblies 60 and 62.

Figure 5:
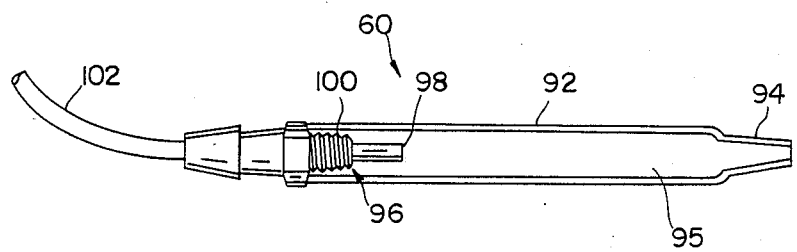
FIG. 5 is an enlarged view, partly broken away and partly in section, of a cartridge electrode employed in the apparatus of FIG. 1.

With reference to FIG. 5, the current electrode cartridge 60 is inserted directly into the bore 56 of the front chamber 44. Cartridge 62 which is substantially identical to cartridge 60 is inserted into the axial bore 86 of chamber 74. The cartridges complete an electrical circuit for passing a test current through the epithelial tissue T from test chamber 44 to test chamber 74.

Cartridge assembly 60 comprises an elongated plastic tube 92 having a forward tapered tip 94. The tapered tip 94 is dimensioned so that the cartridge may be efficiently connected to the chamber by forcibly inserting the tip 94 into bore 56. The tip 94 is preferably semi-resilient to facilitate sealing against the walls of bore 86. The cartridge 60 may be easily disconnected by withdrawing the cartridge tip from the bore.

A threaded female connector 96 is formed at the proximal end of the tube. The tube 92 is filled with a gel material 95 such as agar. Other types of gel materials may also be suitable. The agar gel composite 95 is obtained by filling the tube with a hot salt solution in which two to four percent agar, by weight, has been dissolved. The salt solution is comprised of KCl salt dissolved in distilled water to a concentration of 3 M or more. The high salt concentration insures that the cartridge gel 95 will have a very low electrical resistance. A billet 98 or slug having a silver-silver chloride composition functions as the electrode. The billet 98 screws into tube connector 96. As the agar salt solution cools, the agar gel hardens to encapsulate the billet. A lead wire 102 bonded to the billet 98 and insulated from the electrical gel provides electrical connection with the nearby electrical test apparatus. Cartridge assembly 62 is also connected via lead 106, with the test apparatus to complete the test circuit.

It will be appreciated that the silver-silver chloride employed as an electrode material for billet 98 has a number of advantages, including the exhibition of a very stable voltage when in contact with electrolyte containing chloride ions. The electrode also offers a relatively low electrical resistance to the passage of current and does not become easily polarized when current flows. The billet 98 or slug is made by compressing or sintering silver and silver chloride powder in equal proportions, although the latter specific ratio is not critical. A suitable method for preparing the billet 98 for the electrode cartridge assembly 60 is disclosed in U.S. Pat. No. 3,137,291. It will be further appreciated that the gel filled plastic cartridge is relatively compact and has a low resistance. The cartridge 60 can be quickly installed and removed from the test rack 14. The cartridge is essentially reusable, and therefore can be cleaned of the gel 95 with hot water, and a fresh gel salt solution poured and cast as previously described.

One of the features of rack 14 is that the rack may be easily disassembled to remove the cell culture cups. The clamp screws 25 are loosened, the cover 26 is removed, and the panels 22 and 24 and suspended cups 12 are lifted from the base. The panels are separated from the culture cups. The panels 22 and 24 including the receiving cavities 36 and 38 and associated ports and passages may then be easily sterilize.. The rack components are structured for ready exposure to sterilization fluids.

While a preferred embodiment of the foregoing invention has been set forth for purposes of illustration, the foregoing description should not be deemed a limitation of the invention herein. Accordingly, various modifications, adaptations, and alternatives may occur to one skilled i the art without departing from the spirit and the scope of the present invention.

What is claimed is:

1. Apparatus for electrically testing a specimen disposed on a substrate of a culture cup having opposed first and second ends comprising:

first rack section means defining a first cavity for receiving the first end of said cup to form a first test chamber located on one side of said substrate;

second rack section means defining a second cavity for receiving the second end of said cup to form a second test chamber located on the other side of said substrate;

first irrigation connector means for connecting with a pair of conduits to form an irrigation path through said first chamber;

second irrigation connector means for connecting with a pair of conduits to form an irrigation path through said second chamber;

first cartridge receiving means of receiving a cartridge for communication with said first chamber;

second cartridge receiving means for receiving a cartridge for communication with said second chamber; and clamp means for releasably clamping said first and second rack sections in a cooperative relationship wherein a said cup is receivable in said first and second cavities for retention between said rack sections.

2. The apparatus of claim 1 wherein said first and second rack section means each comprise a panel-like member.

3. The apparatus of claim 1 further comprising sealing means for sealing one end of said cup with a said rack section means in fluid-tight relationship.

4. The apparatus of claim 1 wherein, upon reception of said cup in said first and second cavities, said cup is suspended in transverse relationship between said first and second rack section means.

5. The apparatus of claim 1 wherein said clamp means comprises at least one clamp member having a pair of opposing edges disposed in equidistantly laterally spaced fixed relationship.

6. The apparatus of claim 5 further comprising a pair of clamp members having opposing edges, portions of said first and second rack sections means being engagable against said clamp member edges for interlocking a said culture cup, said first rack section means and said second rack section means.

7. The apparatus of claim 1 wherein said first and second cavities are alignable to define a longitudinal axis, and at least one of said first and second cartridge receiving means comprise means defining an axial bore through a said rack section means into a said test chamber.

8. The apparatus of claim 1 wherein at least one of said irrigation connector means comprises a pair of diametral conduits integrally extending from a said rack means and communicating with a said test chamber.

9. The apparatus of claim 1 and further comprising an electrode cartridge means receivable in a said cartridge receiving means, said electrode cartridge means comprising a cartridge having a proximal end portion and a distal tapered tip, an electrode being disposed in said proximal portion and a gel material substantially filling said cartridge from said proximal end portion to said tapered tip.

10. The apparatus of claim 9 wherein said tapered tip and a said cartridge receiving means are dimensioned to allow insertion of said cartridge means to provide a force fit fluid-tight connection and to permit retraction of said cartridge means from the said cartridge receiving means.

11. The apparatus of claim 1 wherein at least one of said irrigation connector means comprises an inverted generally L-shaped conduit which extends interiorly into a said test chamber.

12. The apparatus of claim 1 wherein said first and second rack section means are substantially panel-like members each defining a stepped-cylindrical receiving cavity and having a generally cylindrical protruding structure surrounding an end of said cavity.

13. The apparatus of claim 12 wherein said first and second cavities are axially dimensioned to receive portions of said cup so that an intermediate portion of said cup is located between said first and second rack sections when the cup is received in said cavities and said clamp means releasably clamps said rack section means in cooperative relationship.

14. Apparatus for electrically testing a plurality of membrane tissues, each membrane tissue being disposed on a substrate of a culture cup, the cup having opposed first and second ends, said apparatus comprising:

first rack section means defining a first array of cavities for receiving the first ends of said cups to form a plurality of first test chambers located on one side of said cup substrates;

second rack section means defining a second array of cavities alignable with said first array of cavities for receiving the second ends of said cups to form a plurality of second test chambers located on the other side of said cup substrates;

first irrigation connector means associated with each first test chamber for connecting with a pair of conduits to form an irrigation path through each of said first test chambers;

electrical current flow circuit path means for establishing an electrical path between each of said alignable first and second test chambers; and clamp means for releasably clamping said first and second rack section means in a cooperative relationship wherein said cups are received in respective aligned cavities of said first and second arrays.

15. The apparatus of claim 14 wherein said electrical path means comprises a plurality of cartridges insertable in said section means for communication with test chambers.

16. The apparatus of claim 14 wherein said clamp means comprises a pair of clamp members, each said clamp member having a pair of equidistantly spaced edges for engaging portions of said first and second rack section means in interlocking relationship.

17. The apparatus of claim 14 wherein each of said first and second rack section mean comprise panel-like members defining an array of cavities having a generally stepped-cylindrical shape.

18. The apparatus of claim 14 further comprising sealing means for sealing each of said cups ends to said rack means.

19. An electrode cartridge assembly for the electrical testing of a specimen comprising:

cartridge means having a proximal end portion and a distal end portion having a tapered tip;

electrode means disposed in said proximal end portion;

connector means for removably connecting said cartridge means and said electrode means; and gel material substantially filling said cartridge from said electrode means to said tapered tip.

20. The assembly of claim 19 wherein said gel material comprises agar gel having a high salt concentration.

21. The assembly of claim 19 wherein said electrode means comprises a billet having a silver-silver chloride composition.

22. The assembly of claim 19 wherein said connector means comprises complementary threaded surfaces at the interior of said cartridge means and the exterior of said electrode means.

23. A method for electrically testing specimens disposed on a substrate of a cell culture cup comprising the steps of:

inserting opposed end portions of a culture cup into cavities defined by a pair of members and clamping said members together to form first and second test chambers, said test chambers respectively being in-part defined by a portion of the cell culture cup disposed on opposite sides of the substrate;

passing a first irrigation stream through said first test chamber;

passing a second irrigation stream through said second test chamber; and establishing an electrical current path through said first test chamber and said second test chamber through the specimen.

24. The assembly of claim 19 wherein the gel material is formed by dissolving a salt in water to form a salt solution having a salt concentration of at least 3 M and dissolving agar in the salt solution to form an agar gel solution.

25. The assembly of claim 19 wherein the gel material is formed by dissolving a salt in water to form a salt solution and dissolving agar in the salt solution to form an agar gel solution, the weight of agar to the salt solution being approximately 2 to 4 percent.

26. The assembly of claim 19 wherein said electrode means comprises:

a mixture of silver and silver chloride.

* * * * *